United States Patent
Matsufuji et al.

(10) Patent No.: US 12,306,135 B2
(45) Date of Patent: May 20, 2025

(54) SENSITIVITY CALIBRATION METHOD, INSPECTION DEVICE, AND MAGNETIC SENSOR GROUP

(71) Applicant: JFE STEEL CORPORATION, Tokyo (JP)

(72) Inventors: Yasuhiro Matsufuji, Tokyo (JP); Takahiro Koshihara, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 179 days.

(21) Appl. No.: 18/003,316

(22) PCT Filed: Jun. 25, 2021

(86) PCT No.: PCT/JP2021/024235
§ 371 (c)(1),
(2) Date: Dec. 26, 2022

(87) PCT Pub. No.: WO2022/004613
PCT Pub. Date: Jan. 6, 2022

(65) Prior Publication Data
US 2023/0258598 A1    Aug. 17, 2023

(30) Foreign Application Priority Data
Jul. 3, 2020 (JP) .................................. 2020-115939

(51) Int. Cl.
*G01N 27/83* (2006.01)
*G01N 33/2045* (2019.01)
*G01R 33/00* (2006.01)

(52) U.S. Cl.
CPC ......... *G01N 27/83* (2013.01); *G01N 33/2045* (2019.01); *G01R 33/0017* (2013.01); *G01R 33/0023* (2013.01); *G01R 33/0035* (2013.01)

(58) Field of Classification Search
CPC ................ G01N 27/83; G01R 33/0017; G01R 33/0023; G01R 33/0035; G01R 33/091; G01R 33/2045
See application file for complete search history.

(56) References Cited

U.S. PATENT DOCUMENTS

| | | | | |
|---|---|---|---|---|
| 4,445,088 A | * | 4/1984 | Schubel | ................ G01N 27/82 324/238 |
| 2003/0042897 A1 | * | 3/2003 | Wolodko | ............... G01N 27/82 324/335 |

(Continued)

FOREIGN PATENT DOCUMENTS

| | | |
|---|---|---|
| CN | 105929019 A | 9/2016 |
| EP | 2717042 A1 | 4/2014 |

(Continued)

OTHER PUBLICATIONS

Translation of JP2018054301 (Year: 2018).*

(Continued)

*Primary Examiner* — Steven L Yeninas

(57) ABSTRACT

An inspection device includes multiple magnetic sensors, wiring for calibration and a controller. The wiring for calibration is arranged at the same relative position with respect to a magnetically sensitive portion of each of the multiple magnetic sensors. The controller obtains a first output value of each of the multiple magnetic sensors in advance. Before a predetermined portion of an electrical steel sheet passes the position of the magnetic sensors, the controller retracts the multiple magnetic sensors. The controller starts applying a current to the wiring for calibration. The controller obtains a second output value of each of the multiple magnetic sensors. After the predetermined position passes, the controller displaces the multiple magnetic sensors to the detection position. The controller corrects a measurement value measured by each of the multiple mag- (Continued)

netic sensors based on the first output value and the second output value.

6 Claims, 7 Drawing Sheets

(56) References Cited

U.S. PATENT DOCUMENTS

| | | | |
|---|---|---|---|
| 2008/0238410 A1* | 10/2008 | Charlier | G01R 33/0206 |
| | | | 324/202 |
| 2011/0031960 A1 | 2/2011 | Hohe et al. | |
| 2020/0041453 A1 | 2/2020 | Fuchsloch et al. | |
| 2021/0025949 A1* | 1/2021 | Gillinger | G01R 33/0035 |

FOREIGN PATENT DOCUMENTS

| | | |
|---|---|---|
| GB | 2490393 A | 10/2012 |
| JP | H0510926 A | 1/1993 |
| JP | H08211023 A | 8/1996 |
| JP | H08327603 A | 12/1996 |
| JP | 2004354282 A | 12/2004 |
| JP | 2005061940 A | 3/2005 |
| JP | 2007057281 A | 3/2007 |
| JP | 2010014701 A | 1/2010 |
| JP | 2013011588 A | 1/2013 |
| JP | 2015135261 A | 7/2015 |
| JP | 2018054301 A | 4/2018 |
| JP | 2018124266 A | 8/2018 |
| JP | 2020510217 A | 4/2020 |

OTHER PUBLICATIONS

Translation of JP2004354282 (Year: 2004).*
Nov. 7, 2023, the Extended European Search Report issued by the European Patent Office in the corresponding European Patent Application No. 21833218.7.
May 16, 2024, Office Action issued by the Korean Intellectual Property Office in the corresponding Korean Patent Application No. 10-2022-7045626 with English language concise statement of relevance.
May 9, 2023, Notification of Reasons for Refusal issued by the Japan Patent Office in the corresponding Japanese Patent Application No. 2021-562190 with English language concise statement of relevance.
Nov. 29, 2022, Notification of Reasons for Refusal issued by the Japan Patent Office in the corresponding Japanese Patent Application No. 2021-562190 with English language Concise Statement of Relevance.
Sep. 14, 2021, International Search Report issued in the International Patent Application No. PCT/JP2021/024235.

* cited by examiner

FIG. 3
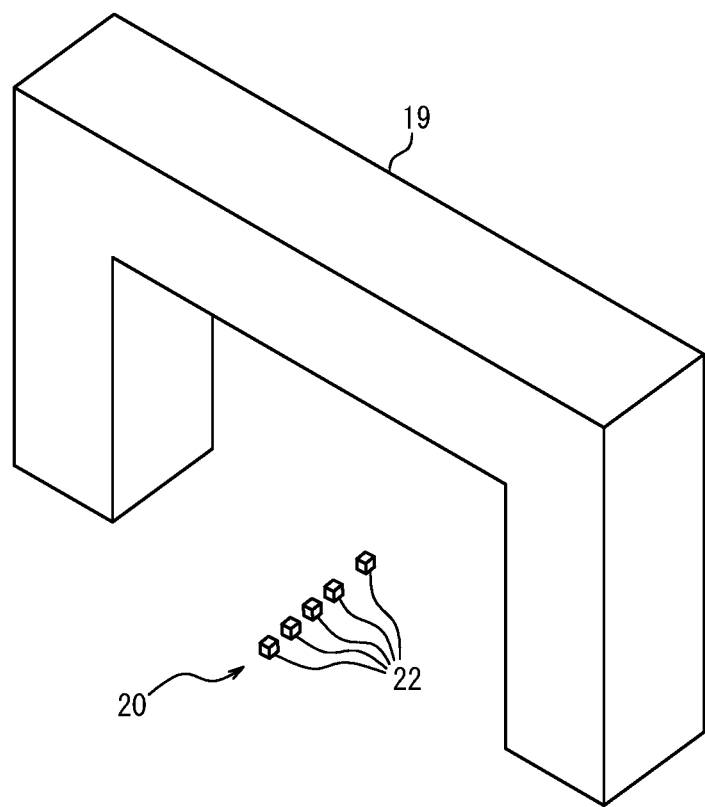
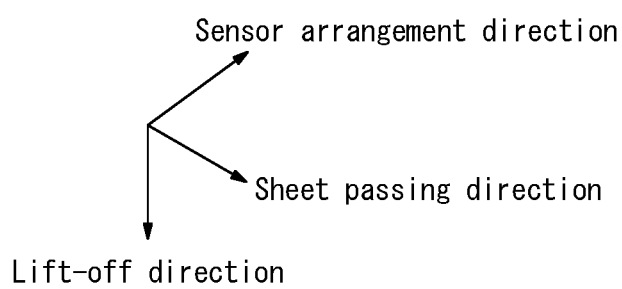

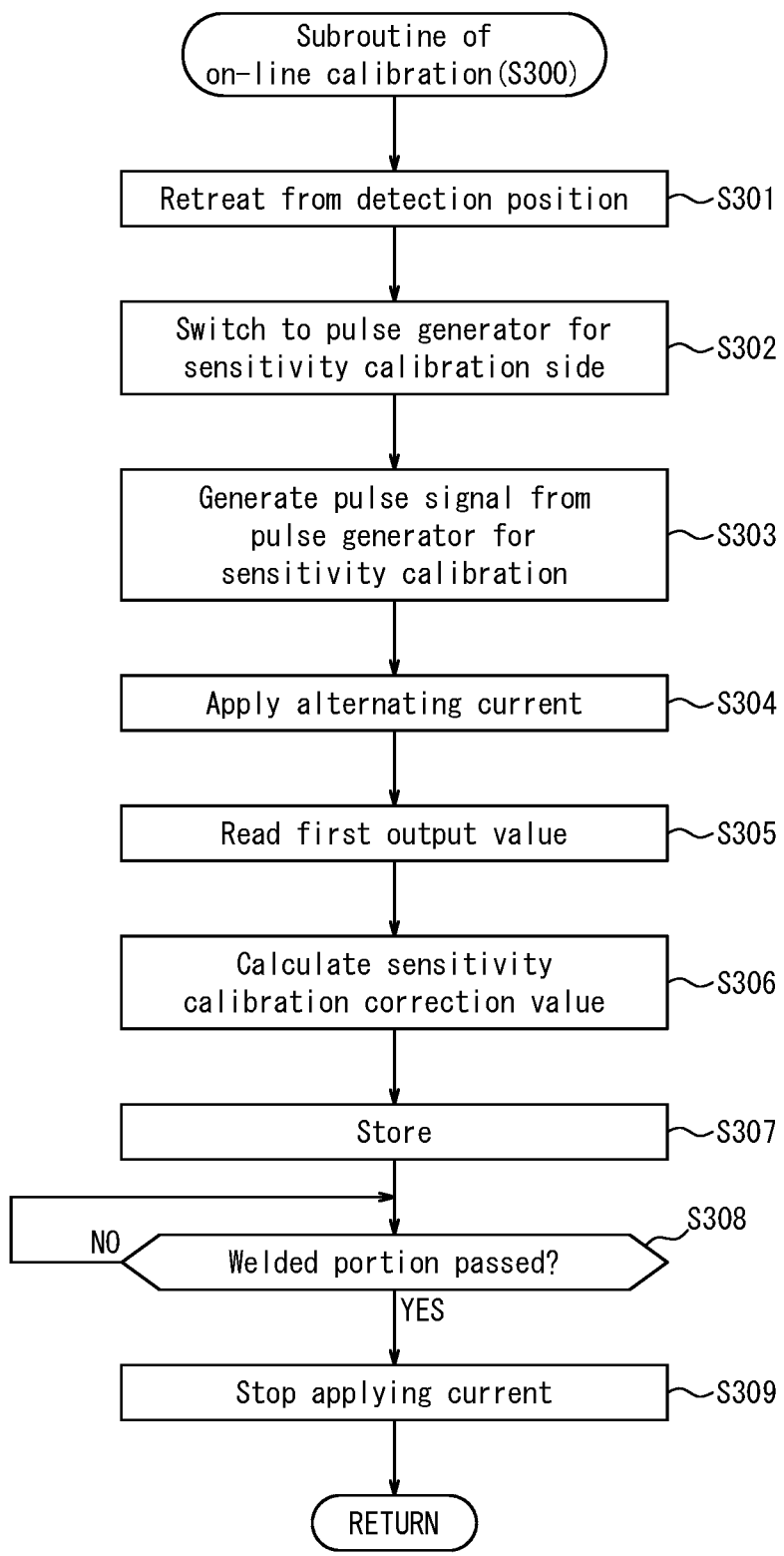

SENSITIVITY CALIBRATION METHOD, INSPECTION DEVICE, AND MAGNETIC SENSOR GROUP

CROSS REFERENCE TO RELATED APPLICATION

This application claims priority to Japanese Patent Application No. 2020-115939 filed on Jul. 3, 2020, the entire disclosure of which is incorporated herein by reference.

TECHNICAL FIELD

This disclosure relates to a sensitivity calibration method of calibrating the sensitivity of multiple magnetic sensors in an inspection device for steel sheet evaluation, an inspection device, and a magnetic sensor group.

BACKGROUND

There are known inspection devices that evaluate steel sheets, such as grain-oriented electrical steel sheets, by magnetizing the steel sheets and detecting leakage flux. For example, there is a known device that measures the electromagnetic properties of a grain-oriented steel sheet to evaluate iron loss in the steel sheet (see JP 2018-124266 A (PTL 1)).

CITATION LIST

Patent Literature

PTL 1: JP 2018-124266 A

SUMMARY

Technical Problem

In a device that measures the electromagnetic properties of a steel sheet, multiple magnetic sensors are arranged on a plane parallel to the sheet surface of the steel sheet to perform measurement all along the width direction of the steel sheet, and each magnetic sensor detects leakage flux. To correctly measure the electromagnetic properties of the entire steel sheet, it is necessary to use magnetic sensors of the same sensitivity. However, there are variations in sensitivity among the multiple magnetic sensors due to temperature change and temporal change, which may cause differences in measurement accuracy. Therefore, it is necessary to adjust the sensitivity of the magnetic sensors accordingly. In many cases, however, the sensitivity is originally different in each magnetic sensor. The sensitivity should be adjusted individually for each magnetic sensor, and examples of adjusting methods include a method of preparing a standard sample and measuring the single standard sample with all sensors. However, the sensitivity adjustment takes time and effort because it is performed while observing the output waveform. Therefore, this method is onerous in a case of multiple sensors. On the other hand, if one tries to calibrate a large number of sensors simultaneously using a single standard sample, the results will be affected by variations in the properties within the standard sample. Further, since sensitivity adjustment cannot be performed when an electrical steel sheet manufacturing line is in operation, the manufacturing line should be temporarily halted for the adjustment, which is undesirable in terms of manufacturing efficiency.

To solve the problems of conventional technologies described above, it could be helpful to provide a sensitivity calibration method with which the sensitivity of magnetic sensors can be calibrated easily and reliably, an inspection device, and a magnetic sensor group.

Solution to Problem

To solve the above problems, a sensitivity calibration method according to a first aspect is a sensitivity calibration method of an inspection device of a steel sheet, comprising multiple magnetic sensors respectively arranged near wiring for calibration for passing an alternating current for calibration, wherein
  the inspection device obtains a first output value of each of the multiple magnetic sensors in advance by applying an alternating current to the wiring for calibration,
  before a predetermined portion of the steel sheet passes a position of the magnetic sensors in a sheet passing direction, the inspection device retracts the multiple magnetic sensors from a detection position of leakage flux of the steel sheet, starts applying an alternating current to the wiring for calibration, and obtains a second output value of each of the multiple magnetic sensors, and
  after the predetermined position passes the position of the magnetic sensors, the inspection device displaces the multiple magnetic sensors to the detection position, and corrects a measurement value measured by each of the multiple magnetic sensors based on the first output value and the second output value.

In a sensitivity calibration method according to a second aspect,
  the wiring for calibration is arranged at a same relative position with respect to a magnetically sensitive portion of each of the multiple magnetic sensors.

In a sensitivity calibration method according to a third aspect,
  each of the multiple magnetic sensors is connected to each of multiple gain-adjustable amplifiers, and
  each of the multiple amplifiers is adjusted in terms of gain so that, in at least one of a state in which the multiple magnetic sensors are retracted from the detection position and a state in which the steel sheet is removed from the sheet passing section, an output value of each of the multiple amplifiers is a same calibration value in a state in which an alternating current is applied to the wiring for calibration.

In a sensitivity calibration method according to a fourth aspect,
  the inspection device performs correction by multiplying a measurement value measured by each of the multiple magnetic sensors by a value obtained by dividing the first output value by the second output value.

An inspection device according to a fifth aspect comprises,
  a sheet passing section for passing a steel sheet,
  a magnetizer that magnetizes the steel sheet,
  multiple magnetic sensors that are arranged at different positions on a plane perpendicular to a lift-off direction and detect leakage flux generated in the steel sheet magnetized by the magnetizer,
  wiring for calibration that is arranged at a same relative position with respect to a magnetically sensitive portion of each of the multiple magnetic sensors,
  an adjustment mechanism that is capable of switching between retraction of the multiple magnetic sensors from a detection position of leakage flux of the steel sheet and displacement of the multiple magnetic sensors to the detection position, and a controller that controls application of an alternating current to the wiring for calibration and driving of the adjustment mechanism, wherein the controller obtains a first output value of each of the multiple magnetic sensors in advance by applying an alternating current to the wiring for calibration, before a predetermined portion of the steel sheet that is passed by the sheet passing section passes a position of the magnetic sensors in a sheet passing direction, the controller retracts the multiple magnetic sensors from a detection position of leakage flux of the steel sheet, starts applying an alternating current to the wiring for calibration, and obtains a second output value of each of the multiple magnetic sensors, and after the predetermined position passes the position of the magnetic sensors, the controller displaces the multiple magnetic sensors to the detection position, and corrects a measurement value measured by each of the multiple magnetic sensors based on the first output value and the second output value.

In an inspection device according to a sixth aspect, the wiring for calibration is arranged at a same relative position with respect to a magnetically sensitive portion of each of the multiple magnetic sensors.

An inspection device of a steel sheet according to a seventh aspect comprises, a sheet passing section for passing a steel sheet, a magnetizer that magnetizes the steel sheet, multiple magnetic sensors that are arranged at different positions on a plane perpendicular to a lift-off direction and detect leakage flux generated in the steel sheet magnetized by the magnetizer, wiring for calibration that is arranged at a same relative position with respect to a magnetically sensitive portion of each of the multiple magnetic sensors, and a controller that controls application of an alternating current to the wiring for calibration.

A magnetic sensor group according to an eighth aspect comprises a circuit board having a magnetic sensor and on which wiring arranged near the magnetic sensors is formed, and at least one set of wiring interconnecting a plurality of the circuit boards.

Advantageous Effect

According to the sensitivity calibration method, inspection device, and magnetic sensor group of the present disclosure configured as described above, sensitivity calibration of magnetic sensors can be performed so as to reduce the decrease in measurement accuracy of electromagnetic properties of an entire electrical steel sheet.

BRIEF DESCRIPTION OF THE DRAWINGS

In the accompanying drawings:

FIG. 3 is an arrangement diagram illustrating the arrangement of multiple magnetic sensors in the magnetizer of FIG. 2;

FIG. 7 is a flowchart that explains a subroutine of on-line calibration performed by the controller in FIG. 2.

DETAILED DESCRIPTION

The following describes embodiments of the present disclosure with reference to the drawings.

Figure 1:
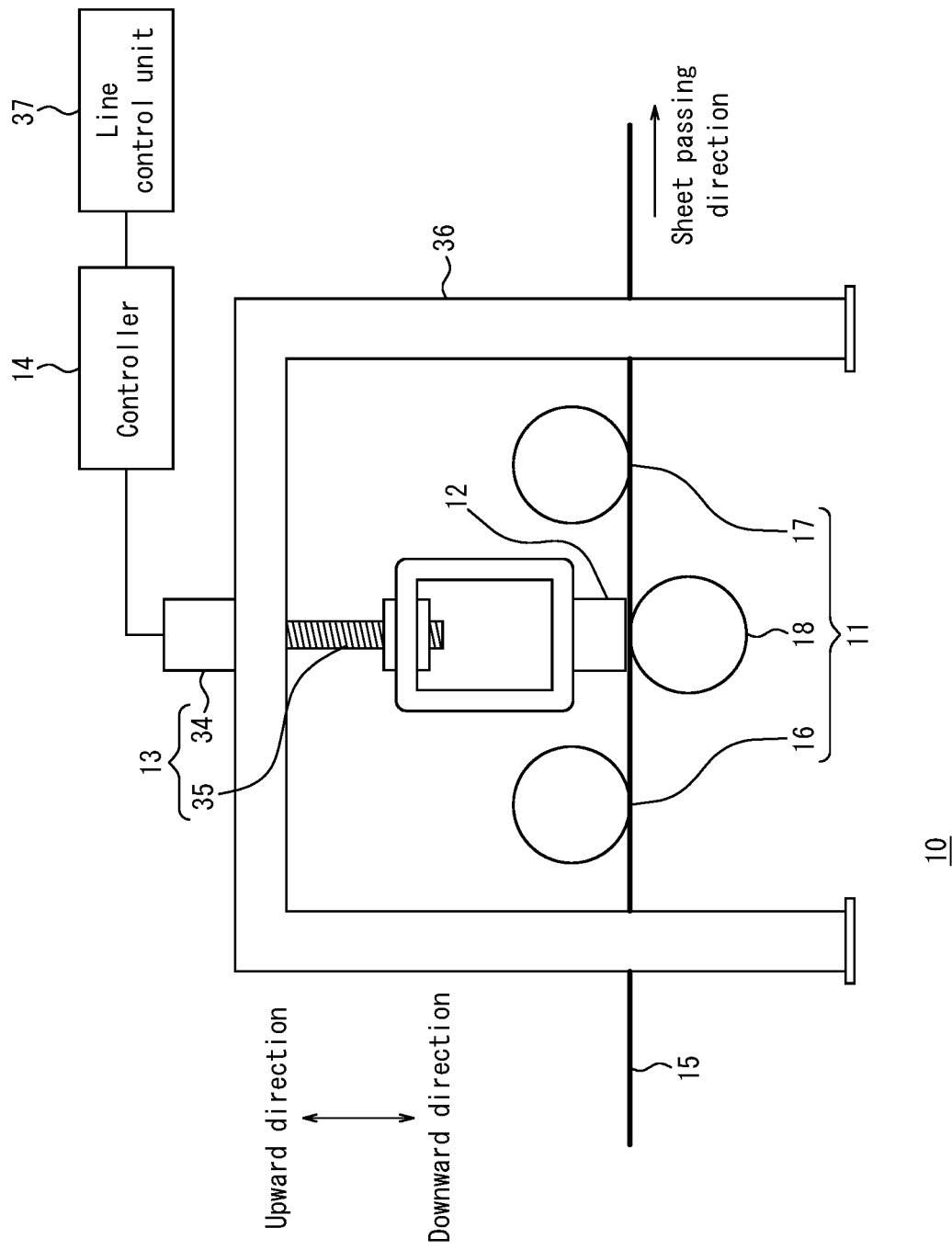
FIG. 1 schematically illustrates an inspection device according to the present embodiment.

FIG. 1 schematically illustrates an inspection device 10 according to an embodiment of the present disclosure. The inspection device 10 includes a sheet passing section 11, a leakage flux detection section 12, an adjustment mechanism 13, and a controller 14. The inspection device 10 evaluates the processing state of a steel sheet in a magnetic domain refining process by measuring the electromagnetic properties of the steel sheet, for example. The upward direction in FIG. 1 is called the upward direction in the inspection device 10, and the downward direction is called the downward direction in the inspection device 10.

The sheet passing section 11 passes a steel sheet 15 in the sheet passing direction parallel to the sheet surface. The steel sheet 15 is, for example, a grain-oriented electrical steel sheet. In the present embodiment, the sheet passing section 11 includes a first passing roller 16, a second passing roller 17, and a third passing roller 18. The first passing roller 16, the second passing roller 17, and the third passing roller 18 are pivoted in parallel with each other. The third passing roller 18 is pivoted below the first passing roller 16 and the second passing roller 17. The steel sheet 15 may be sandwiched between the first passing roller 16 and the second passing roller 17, and the third passing roller 18. At least one of the first passing roller 16, the second passing roller 17, and the third passing roller 18 may be rotated by an electric motor or the like to pass the steel sheet 15 in the sheet passing direction.

The first passing roller 16, the second passing roller 17, and the third passing roller 18 configured as described above prevent contact between the steel sheet 15 and the leakage flux detection section 12 due to fluttering of the steel sheet 15, and noise contamination caused by lift-off fluctuation. The first passing roller 16, the second passing roller 17, and the third passing roller 18 are, for example, rubber rollers. Rubber rollers can prevent slipping between the rollers and the steel sheet 15, and occurrence of magnetic influence on the leakage flux detection section 12.

Figure 2:
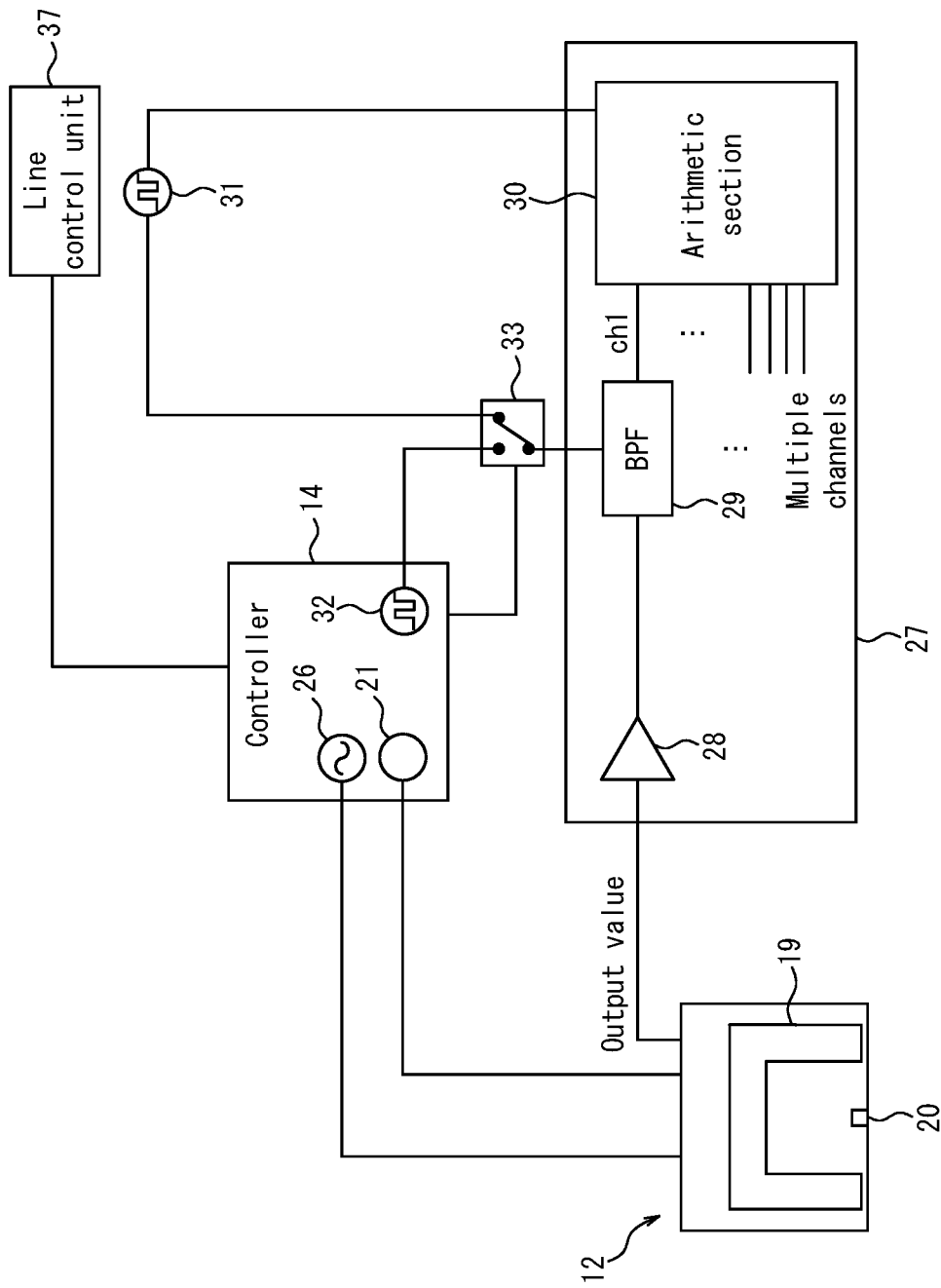
FIG. 2 is a functional block diagram that illustrates a schematic configuration of a signal processing section that performs signal processing on an output value output from the leakage flux detection section in FIG. 1, as well as a schematic configuration of the leakage flux detection section.

As illustrated in FIG. 2, the leakage flux detection section 12 includes a magnetizer 19 and a magnetic sensor group 20.

The magnetizer 19 externally magnetizes the steel sheet 15. The magnetizer 19, for example, externally magnetizes the steel sheet 15 with excitation power supplied from an excitation power supply 21. In the present embodiment, the magnetizer 19 externally magnetizes the steel sheet 15 so that the magnetic domain wall of a magnetic domain in an area where no magnetic domain refining is performed moves, but the direction of magnetization of a magnetic domain in an area where magnetic domain refining has been performed is not parallel to the easy magnetization axis direction.

As illustrated in FIG. 3, the magnetic sensor group 20 includes multiple magnetic sensors 22. The multiple magnetic sensors 22 are arranged between the magnetic poles of the magnetizer 19 at different positions in a plane perpendicular to the lift-off direction, or in other words, in a plane parallel to the sheet surface of the steel sheet 15 that passes in the sheet passing section 11. In the present embodiment, the multiple magnetic sensors 22 are arranged in a straight line along a direction perpendicular to the sheet passing direction in the plane at a predetermined pitch. As used herein, the lift-off refers to the distance between the steel sheet 15 and a surface of the leakage flux detection section 12 that faces the steel sheet 15. Regarding the multiple magnetic sensors 22, five magnetic sensors 22 are regarded as one unit, and one magnetizer 19 is combined with one unit, for example.

The magnetic sensor 22 is, for example, a magnetoresistive element or a Hall element. In the present embodiment, the magnetic sensor 22 is a magnetoresistive element. The magnetic sensor 22 detects leakage flux generated in the steel sheet 15 that has been magnetized by the magnetizer 19. In the present embodiment, each magnetic sensor 22 is arranged to detect the leakage flux component perpendicular to the surface of the steel sheet 15. The magnetic sensor 22 then outputs a leakage flux signal value, such as voltage, corresponding to the detected leakage flux.

Figure 4:
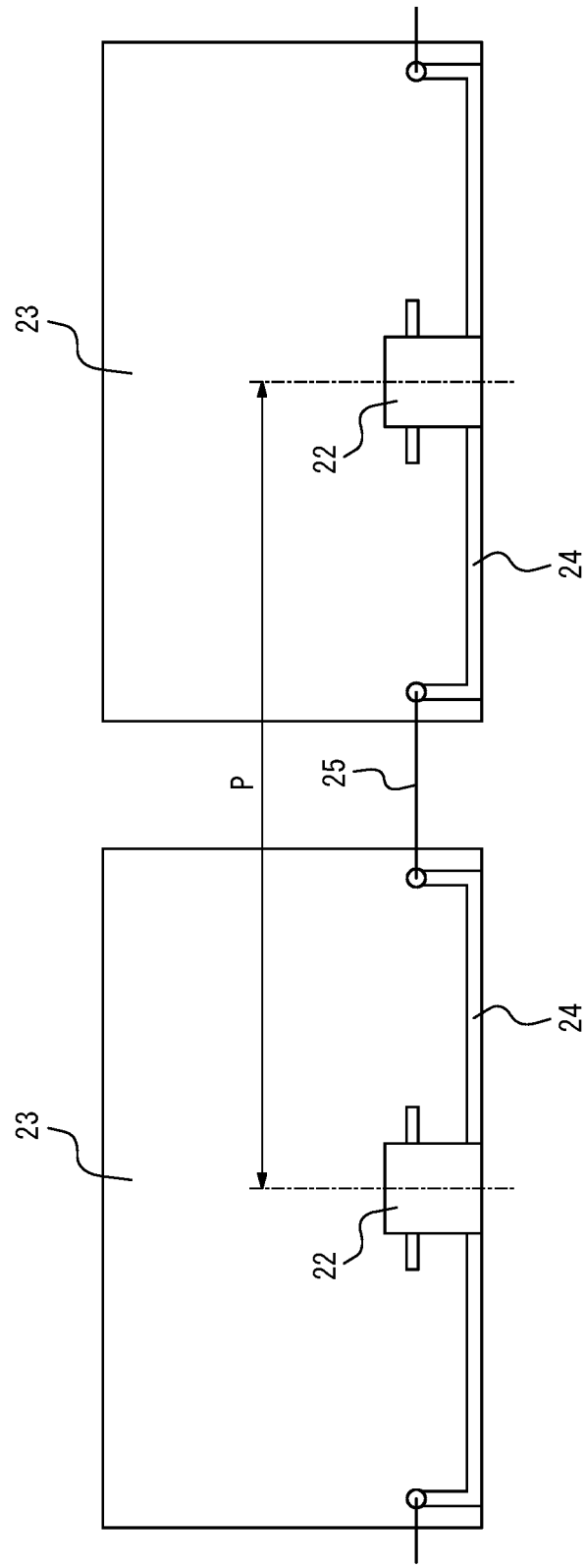
FIG. 4 is an external view of the multiple printed circuit boards provided with a magnetic sensor in FIG. 3.

As illustrated in FIG. 4, each magnetic sensor 22 is mounted on a separate printed circuit board 23 in the present embodiment. In other words, one magnetic sensor 22 is mounted on one printed circuit board 23. Wiring 24 for calibration having a linearly extending portion is provided as a pattern line on the printed circuit board 23. For example, a printed circuit board 23 on which a magnetic sensor 22 using a magnetoresistive element is mounted is provided with wiring 24 for calibration along one side of the rectangle and near the one side. The magnetic sensor 22 is mounted at a position overlapping the wiring 24 for calibration when viewed from the normal direction of the board surface of the printed circuit board 23. Each printed circuit board 23 has the same shape, and the wiring 24 for calibration also has the same shape, depth, and thickness, and is arranged at the same position on each printed circuit board 23. The magnetic sensor 22 is also mounted at the same position on each printed circuit board 23.

In the leakage flux detection section 12, the multiple printed circuit boards 23 on which the magnetic sensors 22 are mounted are arranged so that the sides on which the wiring 24 for calibration is provided are aligned on the same straight line and the board surfaces are parallel to each other. In the leakage flux detection section 12, the multiple printed circuit boards 23 are arranged at a predetermined pitch P. In the leakage flux detection section 12, the multiple printed circuit boards 23 are arranged so that their board surfaces are parallel to the lift-off direction and perpendicular to the sheet passing direction. As illustrated in FIG. 3, in the multiple printed circuit boards 23 in the leakage flux detection section 12, the center line of the magnetic sensors 22 overlaps the center line of the magnetizer 19 when viewed from the sensor arrangement direction in which the multiple magnetic sensors 22 are arranged.

As illustrated in FIG. 4, the wiring 24 for calibration is connected by lead wires 25 between adjacent printed circuit boards 23. As illustrated in FIG. 2, the wiring 24 for calibration on the printed circuit boards 23 at two ends among the multiple printed circuit boards 23 in the leakage flux detection section 12 is connected to an alternating current power supply 26.

The magnetic sensor group 20 is connected to a signal processing section 27. The signal processing section 27 includes multiple amplifiers 28, multiple bandpass filters 29, and an arithmetic section 30. The number of amplifiers 28 and bandpass filters 29 is the number of channels corresponding to the number of magnetic sensors 22 in the magnetic sensor group 20. Each magnetic sensor 22 is connected in series to an amplifier 28 and a bandpass filter 29 in the stated order.

The amplifier 28 amplifies the output value of the magnetic sensor 22. The gain of the amplifier 28 may be adjusted manually by an operator. The bandpass filter 29 removes disturbance noise components from the output value of the magnetic sensor 22 that has been amplified by the amplifier 28 to extract a frequency band to be detected. Each bandpass filter 29 outputs the extracted frequency band to the arithmetic section 30. The bandpass filter 29 receives the extracted frequency band from a pulse generator 32 for sensitivity calibration or a line PLG 31. A pulse signal switcher 33 switches the pulse signal to be input to the bandpass filter 29 from either the pulse generator 32 for sensitivity calibration or the line PLG 31.

The pulse signal output from the pulse generator 32 for sensitivity calibration is determined according to the frequency of an alternating magnetic field generated by the alternating current power supply 26 applying an alternating current to the wiring 24 for calibration. The pulse signal determines the frequency band of the signal corresponding to the alternating magnetic field to be extracted by the bandpass filter 29. The alternating current sent from the alternating current power source 26 to the wiring 24 for calibration is adjusted so that that the magnetic sensor 22 outputs an output value approximately equal to the output value of the magnetic sensor 22 with respect to the leakage flux of the steel sheet 15. The pulse signal output from the line PLG 31 corresponds to a certain pitch of an area where magnetic domain refining has been performed in the sheet passing direction of the steel sheet 15, and the pulse signal determines the frequency band of the leakage flux signal to be extracted by the bandpass filter 29.

The arithmetic section 30 can be connected to a display. Under the control of the controller 14, the arithmetic section 30 transmits leakage flux signals output from each bandpass filter 29 as information to the display. The display shows the amplitude voltage value output from each bandpass filter 29. Under the control of the controller 14, the arithmetic section 30 transmits amplitude voltage values output from each bandpass filter 29 to the controller 14.

Under the control of the controller 14, the arithmetic section 30 conducts the analogue-to-digital conversion of the leakage flux signal extracted by all the bandpass filters 29 for each running pitch of the steel sheet 15 based on the pulse signal output from the line PLG 31. The arithmetic section 30 corrects the leakage flux signal by multiplying the A/D converted leakage flux signal by a sensitivity calibration correction value, based on the on-line calibration described below.

The arithmetic section 30 evaluates the processing state of a portion that has been subjected to magnetic domain refining of the steel sheet 15 based on the corrected leakage flux signal. For example, the arithmetic section 30 may perform evaluation by obtaining the frequency distribution of each channel by performing fast Fourier transform processing on discrete data within a certain interval of each channel. Alternatively, instead of the fast Fourier transform processing, the arithmetic section 30 may perform evaluation by calculating the average of the amplitudes of the sine curves formed by the discrete data within the certain interval.

The adjustment mechanism 13 can retract the magnetic sensor group 20, in other words, the multiple magnetic sensors 22, from the detection position of the leakage flux of the steel sheet 15 or return the magnetic sensor group 20 to the detection position. The detection position is a position where the leakage flux of the steel sheet 15 can be detected, and it may be a position where the distance between the magnetic sensors 22 and the steel sheet 15, that is, the lift-off is adjusted to a predetermined length.

As illustrated in FIG. 1, the adjustment mechanism 13 includes a servomotor 34 and a ball screw 35 in the present embodiment. The servomotor 34 is provided on a holder 36 so that the rotating shaft is parallel to the vertical direction. One end of the ball screw 35 is pivotally supported by the servomotor 34 on the upward side. The other end of the ball screw 35 supports the leakage flux detection section 12. By rotating the servomotor 34, the leakage flux detection section 12 including the magnetic sensor group 20 can be retracted from the detection position or returned to the detection position.

The controller 14 includes at least one processor. The processor may be a general-purpose processor or a dedicated processor specialized for specific processing, but it is not limited to these processors. The dedicated processor may include an application specific integrated circuit (ASIC). The controller 14 may include a programmable logic device (PLD). The PLD may include a field-programmable gate array (FPGA). The controller 14 controls each section of the inspection device 10, including controlling the application of an alternating current to the wiring 24 for calibration, and the driving of the adjustment mechanism 13.

The controller 14 performs off-line calibration and on-line inspection, including on-line calibration, by operation input to an input section including a button, a keyboard, a pointing device, and the like. The control of each section of the inspection device 10 by the controller 14 to perform the off-line calibration, on-line inspection, and on-line calibration is described below.

The off-line calibration is sensitivity adjustment of the magnetic sensors performed when no steel sheet is being manufactured. In other words, the calibration is performed before the manufacture of steel sheets starts or during the maintenance of the manufacturing line.

In the off-line calibration, the controller 14 controls the pulse signal switcher 33 to switch the pulse signal to be input to the bandpass filter 29 to the side of the pulse generator 32 for sensitivity calibration. The controller 14 controls the pulse generator 32 for sensitivity calibration to generate a pulse signal. By outputting a pulse signal from the pulse generator 32 for sensitivity calibration to the bandpass filter 29, the bandpass filter 29 can extract, from the voltage signal output from the amplifier 28, the same band component as the frequency band of the alternating magnetic field applied to the wiring 24 for calibration.

In the off-line calibration, the controller 14 further controls the alternating current power supply 26 to apply an alternating current to the wiring 24 for calibration. A concentric alternating magnetic field is generated around the wiring 24 for calibration by applying the alternating current. The value of the alternating current at this time is used as a reference current value. Each magnetic sensor 22 detects vertical components of the generated alternating magnetic field. Each magnetic sensor 22 outputs a value corresponding to the detected alternating magnetic field. The output value is amplified by the amplifier and sent to the bandpass filter 29. A signal output by the bandpass filter 29 is displayed, for example, on a display connected to the arithmetic section 30.

The wiring 24 for calibration on the printed circuit boards 23 has the same shape, and the printed circuit boards 23 are connected to each other by lead wires 25. Therefore, if the alternating current has the same value, the same alternating magnetic field is generated in each printed circuit board 23. The value of a magnetic flux of the alternating magnetic field is theoretically determined by the value of the alternating current, and therefore the sensitivity of the magnetic sensor 22 can be adjusted by detecting the magnetic flux with the magnetic sensor and determining its difference from the theoretical value.

In the off-line calibration, the gain of each amplifier 28 is adjusted by the value output by each bandpass filter 29 on the display under the control described above, thereby adjusting the sensitivity of each magnetic sensor 22. The sensitivity adjustment may be performed automatically or by an operator. Each of the amplifiers 28 is adjusted in terms of gain so that their output values are the same calibration value.

As used herein, the output value output by each amplifier 28 is referred to as a first output value, and the adjusted gain value of each amplifier 28 is referred to as a first adjustment value. The first output value itself is represented by V1, and the respective first output values of each of the amplifiers 28 are represented by $V1_1, V1_2, \ldots,$ and $V1_n$ (where n is the number of the magnetic sensors). The gain of the amplifier 28 that outputs the same calibration value is represented by $\alpha1$ as a first adjustment value, and the respective first adjustment values of each of the amplifiers 28 are represented by $\alpha1_1, \alpha1_2, \ldots,$ and $\alpha1_n$ (where n is the number of the magnetic sensors). The first output value V1 at each amplifier 28 may be adjusted to be exactly the same calibration value. Alternatively, the first output values may be not strictly equal to each other, meaning $V1 \approx V1_1 \approx V1_2 \approx \ldots \approx V1_n$ (where n is the number of the magnetic sensors). They may be not strictly equal to each other, especially if the adjustment is performed manually by an operator. As used herein, the first output value V1 may be the average of the respective first output values of each of the amplifiers 28 after gain adjustment.

When the input section detects an operation input to end the off-line calibration, the controller 14 controls the arithmetic section 30 so as to transmit the first output value, which is the calibration value, to the controller 14 as information. The controller 14 stores the first output value received as information in the memory of the controller 14. Further, the controller 14 controls the alternating current power supply 26 so as to stop applying an alternating current to the wiring 24 for calibration.

The leakage flux of the steel sheet is measured using the magnetic sensor 22 that has been calibrated as described above. The measurement of the leakage flux is an on-line inspection performed while passing the steel sheet.

In the on-line inspection, the controller 14 requests a line control unit 37 to transmit the thickness information of the steel sheet 15 to be measured. The controller 14 controls the adjustment mechanism 13 so that the distance between the steel sheet 15 and the leakage flux detection section 12 is a predetermined lift-off based on the thickness information received from the line control unit 37.

In the on-line inspection, the controller 14 further controls the pulse signal switcher 33 to switch the pulse signal to be input to the bandpass filter 29 to the side of the line PLG 31. By outputting a pulse signal from the line PLG 31 to the bandpass filter 29, the bandpass filter 29 can extract, from the voltage signal output from the amplifier 28, the same band component as the frequency band of the leakage flux signal.

In the on-line inspection, the controller 14 further controls the excitation power supply 21 to apply a current for excitation to the magnetizer 19. The excitation current causes the magnetizer 19 to externally magnetize the steel sheet 15. In this state, when the steel sheet 15 is passed by the sheet passing section 11 to the leakage flux detection section 12, the leakage flux generated in the magnetized steel sheet 15 is detected. The detected leakage flux signal is amplified by the amplifier 28, the disturbance noise components are removed by the bandpass filter 29, and the signal is input to the arithmetic section 30.

The on-line calibration is sensitivity adjustment of the magnetic sensors performed during the on-line inspection. The on-line calibration can be performed, for example, when a predetermined portion of the steel sheet passes through the leakage flux detection section 12.

During the on-line inspection, the controller 14 receives information of the position of the predetermined portion of the steel sheet 15 in the sheet passing direction. The predetermined portion may be an arbitrarily defined portion, and it is preferably a portion such as a welded portion where the magnetic sensors 22 are required to be retracted, for example. The welded portion is a welded portion when two steel strips are connected by welding. The position of the predetermined portion of the steel sheet 15 in the sheet passing direction is determined, for example, based on the position of the predetermined portion in an image captured by a camera fixed at a specific position with a specific pose with respect to the holder 36, or the position of the predetermined portion transmitted from the line control unit 37 and the sheet passing speed of the sheet passing section 11.

The controller 14 starts the on-line calibration when the predetermined portion in the sheet passing direction reaches a predetermined position before passing the magnetic sensors 22. In the on-line calibration, the controller 14 controls the adjustment mechanism 13 to retract the leakage flux detection section 12 from the detection position before the position of the predetermined portion in the sheet passing direction passes the position of the leakage flux detection section 12 including the magnetic sensors 22.

In the on-line calibration, the controller 14 further controls the pulse signal switcher 33 to switch the pulse signal to be input to the bandpass filter 29 to the side of the pulse generator 32 for sensitivity calibration. The controller 14 controls the pulse generator 32 for sensitivity calibration to generate a pulse signal. By outputting a pulse signal from the pulse generator 32 for sensitivity calibration to the bandpass filter 29, the bandpass filter 29 extracts, from the voltage signal output from the amplifier 28, the same band component as the frequency band of the alternating magnetic field applied to the wiring 24 for calibration.

In the on-line calibration, the controller 14 controls the alternating current power supply 26 so that a predetermined reference current value is applied to the wiring 24 for calibration of each magnetic sensor 22, as in the off-line calibration. A concentric alternating magnetic field is generated around the wiring 24 for calibration by applying an alternating current, and each magnetic sensor 22 detects vertical components of the alternating magnetic field.

Each magnetic sensor 22 outputs a value corresponding to the detected alternating magnetic field from the detected vertical components of the alternating magnetic field, and the output value is amplified by each amplifier 28 and sent to the bandpass filter 29. The output value of each amplifier 28 at this time is called a second output value. The second output value itself is represented by V2, and the respective second output values of each of the amplifiers 28 are represented by $V2_1$, $V2_2$, ..., and $V2_n$ (where n is the number of the magnetic sensors).

In the on-line calibration, the controller 14 further controls the arithmetic section 30 to transmit the second output value, which has been amplified by the amplifier 28 and removed of disturbance noise by the bandpass filter 29, to the controller 14 as information. The controller 14 calculates a sensitivity calibration correction value for each bandpass filter 29 by dividing the first output value stored in the memory of the controller 14 by the second output value received as information. The controller 14 may use an average value obtained by sampling the second output value for a certain period of time to calculate the sensitivity calibration correction value. The controller 14 stores the calculated sensitivity calibration correction value in the memory of the controller 14 so as to be identifiable for each bandpass filter 29.

When the position of the predetermined portion in the sheet passing direction reaches a position after passing the magnetic sensors 22, the controller 14 controls the alternating current power supply 26 so as to stop applying an alternating current to the wiring 24 for calibration. The controller 14 controls the adjustment mechanism 13 to displace the leakage flux detection section 12 to the detection position. The controller 14 ends the on-line calibration after controlling the adjustment mechanism 13 and resumes the on-line inspection.

In general, a welded portion, which is an example of the predetermined portion, deforms the steel sheet because the welded portion swells, which causes problems such as damage to the magnetic sensors 22. If the on-line calibration is performed when the leakage flux detection section 12 is retracted to a safe place, there is no need to spare time for calibration, which is advantageous in terms of productivity. It is possible to slow down the steel sheet passing speed during the on-line calibration or take other measures so that the on-line calibration can be completed while the predetermined portion is being passed. By performing the on-line calibration each time the predetermined portion passes the leakage flux detection section 12, the frequency of calibration of the magnetic sensors 22 is increased, and the measurement accuracy of the steel sheet can be maintained at a high level.

Here, the sensitivity of the magnetic sensor 22 may deviate from the sensitivity at the time of off-line calibration due to temperature change, temporal change, or other reasons, in other words, the first output value V1 may be not equal to the second output value $V2_n$. Therefore, the output value B of each amplifier 22 in the resumed on-line inspection is adjusted using the sensitivity calibration correction value for each bandpass filter 29 calculated using V1 and $V2_n$. Specifically, $B'=B\times(V1/V2_n)$ can be used to reflect the result of the on-line calibration of the magnetic sensor.

Further, because the difference between the first output value V1 and the second output value $V2_n$ with respect to the reference current value becomes clear during the on-line calibration, it is possible to adjust the gain of each amplifier 28 in the off-line calibration after the on-line calibration. The second adjustment value α2 may be used to adjust the gain of each amplifier 28 so that the value of the resumed on-line inspection is correct. For example, the second adjustment value α2 is calculated for each bandpass filter 29 by multiplying the first adjustment value α1 by the sensitivity calibration correction value (V1/V2$_n$), and the gain adjustment of the amplifier 28 is performed using the calculated value. In this case, the sensitivity calibration correction value may be reset to 1, for example.

Figure 5:
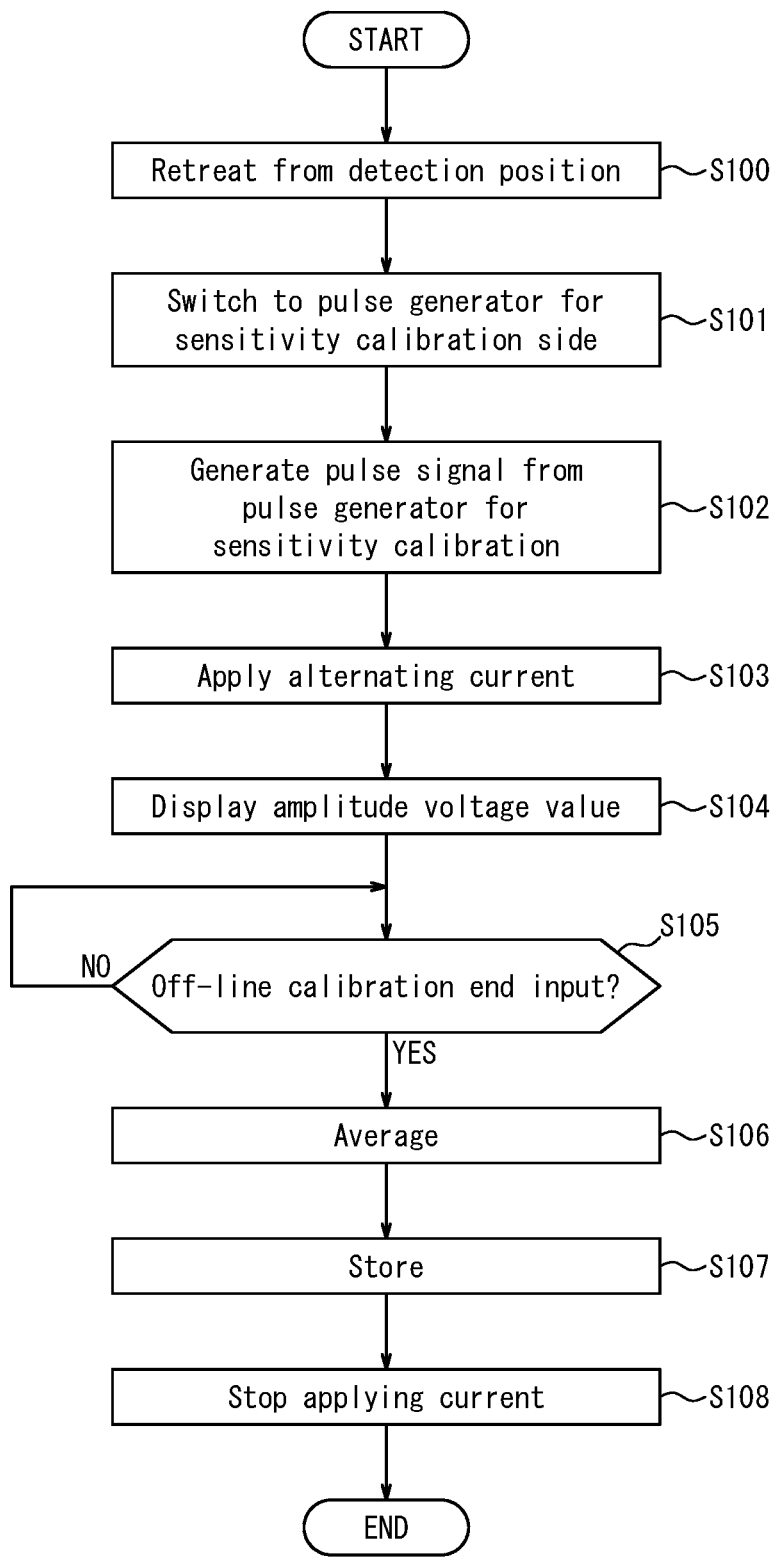
FIG. 5 is a flowchart that explains an off-line calibration process performed by the controller in FIG. 2.

Next, the off-line calibration process performed by the controller 14 in the present embodiment will be described using the flowchart in FIG. 5. The off-line calibration process starts when the input section of the controller 14 detects an operation input that requires the off-line calibration.

In step S100, the controller 14 drives the adjustment mechanism 13 so that the leakage flux detection section 12 is retracted from the detection position. After driving the adjustment mechanism 13, the process proceeds to step S101.

In step S101, the controller 14 controls the pulse signal switcher 33 to switch the pulse signal to be input to the bandpass filter 29 to the side of the pulse generator 32 for sensitivity calibration. After the switching, the process proceeds to step S102.

In step S102, the controller 14 controls the pulse generator 32 for sensitivity calibration to generate a pulse signal. After the generation, the process proceeds to step S103.

In step S103, the controller 14 further controls the alternating current power supply 26 to apply an alternating current to the wiring 24 for calibration. After the application starts, the process proceeds to step S104.

In step S104, the controller 14 controls the arithmetic section 30 so that the output value output from each magnetic sensor 22 is amplified by the amplifier 28, and the amplitude voltage value from which disturbance noise has been removed by the bandpass filter 29 is displayed on the display. After the display starts, the process proceeds to step S105.

In step S105, the controller 14 determines whether or not the input section detects an operation input to end the off-line calibration. Note that when the amplitude voltage value in step S104 is displayed on the display, it is assumed that the gain is adjusted, for example, by manual operation so that the output value of each bandpass filter 29 is the first output value V1. Further, it is assumed that a user will perform an operation input to end the off-line calibration after the gain adjustment is completed. If there is no operation input, the process returns to step S105. If there is an operation input, the process proceeds to step S106.

In step S106, the controller 14 averages all amplitude voltage values output from all the bandpass filters 29 received from the arithmetic section 30 to calculate the first output value. After the calculation, the process proceeds to step S107.

In step S107, the controller 14 stores the first output value calculated in step S106 in the memory of the controller 14. After the storage, the process proceeds to step S108.

In step S108, the controller 14 controls the alternating current power supply 26 so as to stop applying an alternating current to the wiring 24 for calibration. After the application is stopped, the off-line calibration process ends.

Figure 6:
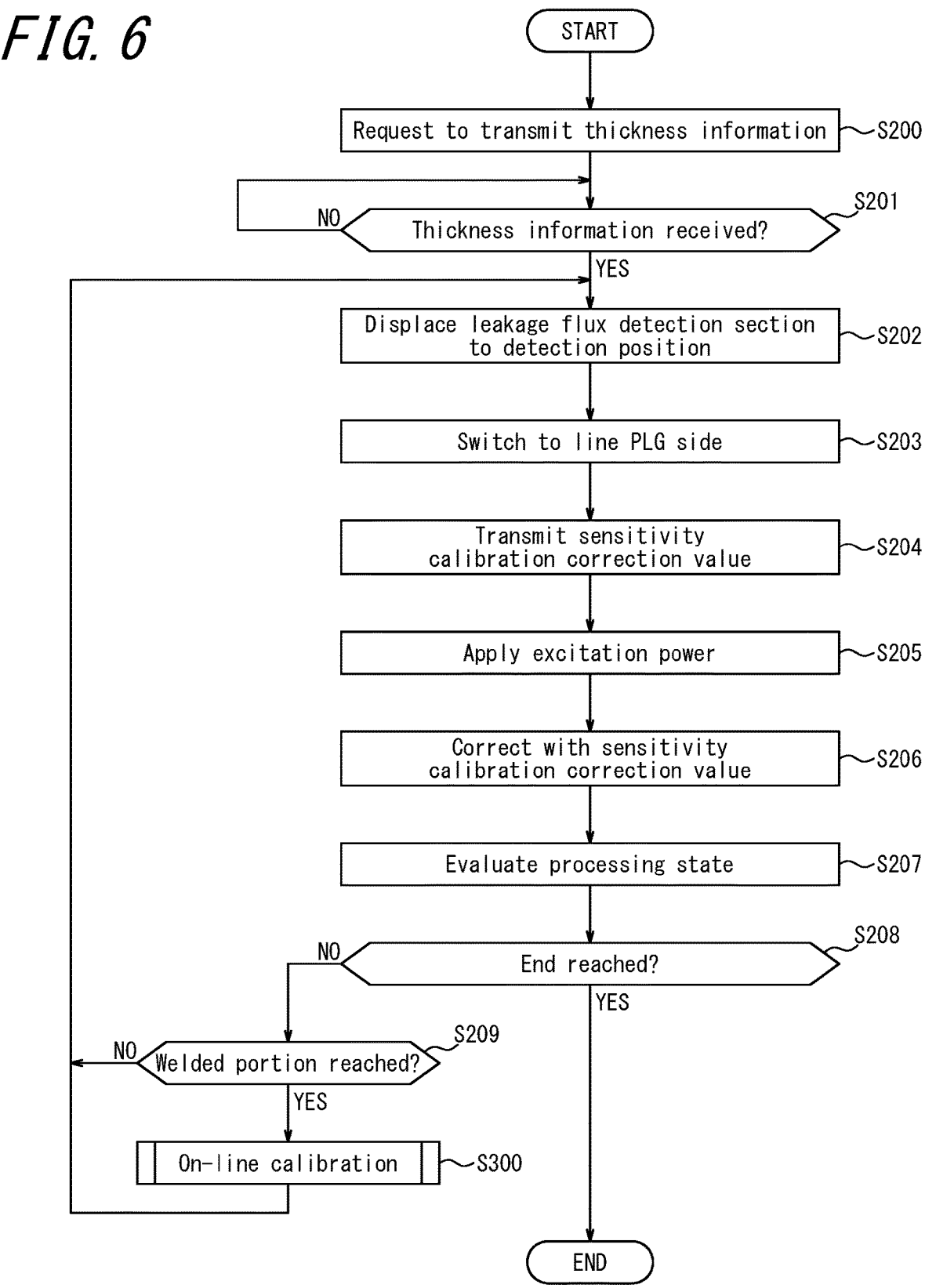
FIG. 6 is a flowchart that explains an on-line inspection process performed by the controller in FIG. 2.

Next, the on-line inspection process performed by the controller 14 in the present embodiment will be described using the flowchart in FIG. 6. The on-line inspection process starts when the input section of the controller 14 detects an operation input that requires the on-line inspection.

In step S200, the controller 14 controls the line control unit 37 to transmit the thickness information of the steel sheet 15 to be rolled onto the sheet passing section 11. After the transmission, the process proceeds to step S201.

In step S201, the controller 14 determines whether or not the thickness information has been received from the line control unit 37. If not received, the process returns to step S201. If received, the process proceeds to step S202.

In step S202, the controller 14 controls the adjustment mechanism 13 to lower the leakage flux detection section 12 to the detection position, which is a predetermined lift-off, based on the thickness information whose reception has been confirmed in step S201.

In step S203, the controller 14 controls the pulse signal switcher 33 to switch the pulse signal to be input to the bandpass filter 29 to the side of the line PLG 31. After the switching, the process proceeds to step S204.

In step S204, the controller 14 transmits the sensitivity calibration correction value stored in the memory of the controller 14 to the arithmetic section 30. After the transmission, the process proceeds to step S205.

In step S205, the controller 14 controls the excitation power source 21 to apply excitation power to the magnetizer 19. After the application, the process proceeds to step S206.

In step S206, the controller 14 controls the arithmetic section 30 to perform correction by multiplying the leakage flux signal, which has been detected by each magnetic sensor 22, amplified by the amplifier 28, and removed of disturbance noise by the bandpass filter 29, by the sensitivity calibration correction value for each bandpass filter 29 transmitted in step S204. After the correction, the process proceeds to step S207.

In step S207, the controller 14 controls the arithmetic section 30 to evaluate the processing state of a portion that has been subjected to magnetic domain refining of the steel sheet 15 based on the leakage flux signal corrected in step S206. After the evaluation, the process proceeds to step S208.

In step S208, the controller 14 determines whether or not the end of the steel sheet 15 has reached the leakage flux detection section 12. If the end has reached, the on-line inspection process ends. If the end has not reached, the process proceeds to step S209.

In step S209, the controller 14 determines whether or not the predetermined portion of the steel sheet 15 has reached the position before passing the magnetic sensors 22. If it has not reached, the process returns to step S202. If it has reached, the subroutine S300 of on-line calibration starts.

Next, the subroutine S300 of on-line calibration performed by the controller 14 in the present embodiment will be described using the flowchart in FIG. 7.

In steps S301 to S304, the controller 14 performs the same control as in steps S100 to S103 in the off-line calibration process. After applying an alternating current in step S304, the process proceeds to step S305.

In step S305, the controller 14 reads the first output value from the memory of the controller 14. After the reading, the process proceeds to step S306.

In step S306, the controller 14 calculates a sensitivity calibration correction value for each bandpass filter 29 by dividing the first output value read in step S305 by the second output value, which has been output from each magnetic sensor 22, amplified by the amplifier 28, and removed of disturbance noise by the bandpass filter 29. After the calculation, the process proceeds to step S307.

In step S307, the controller 14 stores the sensitivity calibration correction value calculated in step S306 in the memory of the controller 14. After the storage, the process proceeds to step S308.

In step S308, the controller 14 determines whether or not the predetermined portion of the steel sheet 15 has passed the position of the magnetic sensors 22. If it has not passed, the process returns to step S308. If it has passed, the process proceeds to step S309.

In step S309, the controller 14 controls the alternating current power supply 26 so as to stop applying an alternating current to the wiring 24 for calibration. After the application is stopped, the subroutine process of on-line calibration ends, and the process returns to step S202.

The inspection device 10 of the present embodiment having the configuration as described above obtains a first output value of each of the multiple magnetic sensors in advance by applying an alternating current to the wiring 24 for calibration. Before the predetermined portion of the steel sheet 15 passes the position of the magnetic sensors 22 in the sheet passing direction, the inspection device 10 retracts the magnetic sensors 22 from the detection position, starts applying an alternating current to the wiring 24 for calibration, and obtains a second output value of each of the multiple magnetic sensors 22. After the predetermined position passes the position of the magnetic sensors 22, the inspection device 10 displaces the magnetic sensors 22 to the detection position, and corrects the measurement value measured by each of the multiple magnetic sensors 22 based on the first output value and the second output value. To obtain good detection sensitivity, the magnetic sensors 22 are generally positioned at a detection position where the lift-off is small during detection of leakage flux of the steel sheet 15. On the other hand, the magnetic sensors 22 are retracted from the detection position when the predetermined portion passes because, for example, the swelling caused by welding or the like may be larger than the lift-off. With the configuration as described above, the inspection device 10 performs the sensitivity calibration of the magnetic sensors 22 at a frequency of passing of the predetermined portion, which is a relatively high frequency, while the electromagnetic properties of the steel sheet 15 are being inspected. Therefore, the inspection device 10 can calibrate the sensitivity of the magnetic sensors 22 so as to reduce the decrease in measurement accuracy of the electromagnetic properties of the entire steel sheet 15.

In the inspection device 10 of the present embodiment, the wiring 24 for calibration is arranged at the same relative position with respect to a magnetically sensitive portion of each of the multiple magnetic sensors 22. With such a configuration, the inspection device 10 can precisely calibrate the sensitivity among the multiple magnetic sensors 22.

In the inspection device 10 of the present embodiment, each of the multiple magnetic sensors 22 is connected to each of the multiple gain-adjustable amplifiers, and each of the multiple amplifiers 28 is adjusted in terms of gain so that, in at least one of a state in which the multiple magnetic sensors 22 are retracted from the detection position and a state in which the steel sheet 15 is removed from the sheet passing section 11, the first output value V1 of each of the multiple amplifiers 28 is the same calibration value. This configuration allows the inspection device 10 to calibrate the sensitivity more precisely.

The inspection device 10 of the present embodiment corrects the measurement value by multiplying the measurement value measured by each of the magnetic sensors 22 in the on-line inspection by the sensitivity calibration correction value, which is obtained by dividing the first output value V1 by the second output value $V2_n$ output from the magnetic sensor 22 in the on-line calibration. With such a configuration, the inspection device 10 can appropriately set the first calibration value V1 by an off-line calibration operator, so that the correction value of the measurement value after the on-line calibration is in a suitable range for measuring the electromagnetic properties of the steel sheet 15.

Although the present disclosure has been described with reference to the drawings and examples, it should be noted that various variations and/or modifications will be readily apparent to those skilled in the art based on the present disclosure. Therefore, it should be noted that these variations and/or modifications are included within the scope of the present disclosure. For example, functions included in each component or the like can be rearranged as long as they are logically consistent, and multiple components can be combined into one set or divided.

For example, in the present embodiment, one printed circuit board 23 is mounted with one magnetic sensor 22. However, one printed circuit board 23 may be mounted with multiple magnetic sensors 22, or one printed circuit board 23 may be mounted with all magnetic sensors 22.

The magnetic sensors 22 may be arranged in one row in the width direction of the steel sheet 15 (the direction perpendicular to the traveling direction), or they may be arranged in multiple rows in the width direction of the steel sheet 15. In this case, if the magnetic sensors 22 are arranged in a staggered arrangement with each other when viewed from above, the inspection can be performed all along the width direction of the steel sheet 15 without gaps, which is more preferable. However, since the magnetic sensors 22 are connected to each other by wiring, it is preferable to arrange a group of magnetic sensors aligned in one row in multiple rows when arranging them in multiple rows. It is also acceptable if all the magnetic sensors 22 can be connected continuously as in a single stroke.

In the present embodiment, the controller 14 retracts the leakage flux detection section 12 from the detection position when performing the off-line calibration, but the leakage flux detection section 12 may not be retracted. Even if the leakage flux detection section 12 is not retracted from the detection position, the gain adjustment of the amplifier 28 can be performed with the steel sheet 15 removed from the sheet passing section 11 to obtain the same effects as in the present embodiment.

In the present embodiment, it is calibration where, when performing the on-line calibration, the controller 14 controls to calculate a sensitivity calibration correction value and store it in the memory of the arithmetic section 30. However, it is also possible to store the second output value V2 in the on-line calibration in the memory and to calculate a sensitivity calibration correction value when performing the subsequent on-line inspection. In the present embodiment, it is calibration where the controller 14 controls the arithmetic section 30 to calculate a sensitivity calibration correction value. However, the controller 14 may calculate a sensitivity calibration correction value and transmit it to the arithmetic section 30.

In the present embodiment, the controller 14 corrects the measurement value in the on-line calibration by multiplying the measurement value by the sensitivity calibration correction value calculated using the first output value V1 that has been adjusted to the same calibration value in the on-line inspection. However, the first output values may not be adjusted to the same calibration value. For example, the measurement value of the signal output from the magnetic sensor 22 may be corrected during the on-line inspection based on the second output value of the signal output from the magnetic sensor 22 in the on-line calibration, without performing the off-line calibration.

In the present embodiment, the controller 14 calculates a sensitivity calibration correction value. However, the calculation may be performed by the arithmetic section 30 based on the control of the controller 14. In the present embodiment, the first output value V1 and the sensitivity calibration correction value are stored in the memory of the controller 14. However, they may be stored in the memory of the arithmetic section 30.

REFERENCE SIGNS LIST

- 10 inspection device
- 11 sheet passing section
- 12 leakage flux detection section
- 13 adjustment mechanism
- 14 controller
- 15 steel sheet
- 16 first passing roller
- 17 second passing roller
- 18 third passing roller
- 19 magnetizer
- 20 magnetic sensor group
- 21 excitation power supply
- 22 magnetic sensor
- 23 printed circuit board
- 24 wiring for calibration
- 25 lead wire
- 26 alternating current power supply
- 27 signal processing section
- 28 amplifier
- 29 bandpass filter
- 30 arithmetic section
- 31 line PLG
- 32 pulse generator for sensitivity calibration
- 33 pulse signal switcher
- 34 servomotor
- 35 ball screw
- 36 holder
- 37 line control unit

The invention claimed is:

1. A sensitivity calibration method of an inspection device performing an on-line inspection, the inspection device measuring leakage of flux of a steel sheet connected by a welded portion while passing the steel sheet in the on-line inspection, the inspection device comprising multiple magnetic sensors respectively arranged near wiring for calibration for passing an alternating current for calibration, wherein each of the multiple magnetic sensors is connected in series to each of multiple gain-adjustable amplifiers and each of a bandpass filters extracting a frequency band to be detected, the inspection device, while the steel sheet is not passed, obtains a first output value of each of multiple magnetic sensors in advance by applying an alternating current to the wiring for calibration and inputting a pulse signal determining a frequency band corresponding to an alternating magnetic field generated by applying an alternating current to the bandpass filter, before a welding portion of the steel sheet passes a position of the magnetic sensors in a sheet passing direction during passing the steel sheet, the inspection device retracts the multiple magnetic sensors from a detection position of leakage flux of the steel sheet, starts applying an alternating current to the wiring for calibration, inputting the pulse signal determining a frequency band corresponding to the alternating magnetic field generated by applying an alternating current to the bandpass filter, and obtains a second output value of each of the multiple magnetic sensors, and after the welding position passes the position of the magnetic sensors during passing the steel sheet, the inspection device displaces the multiple magnetic sensors to the detection position, inputting the pulse signal corresponding to a certain pitch of an area where magnetic domain refining has been performed in the sheet passing direction of the steel sheet, and corrects a measurement value measured by each of the multiple magnetic sensors based on the first output value and the second output value.

2. The sensitivity calibration method according to claim 1, wherein
the wiring for calibration is arranged at a same relative position with respect to a magnetically sensitive portion of each of multiple magnetic sensors.

3. The sensitivity calibration method according to claim 1, wherein
each of the multiple amplifiers is adjusted in terms of gain so that, in at least one of a state in which the multiple magnetic sensors are retracted from the detection position and a state in which the steel sheet is removed from the sheet passing section, a first output value of each of the multiple amplifiers is a same calibration value.

4. The sensitivity calibration method according to claim 1, wherein
the inspection device performs correction by multiplying a measurement value measured by each of the multiple magnetic sensors by a value obtained by dividing the first output value by the second output value.

5. An inspection device, comprising
a sheet passing section for passing a steel sheet,
a magnetizer that magnetizes the steel sheet,
multiple magnetic sensors that are arranged at different positions on a plane perpendicular to a lift-off direction and detect leakage flux generated in the steel sheet magnetized by the magnetizer,
wiring for calibration that is arranged at a same relative position with respect to a magnetically sensitive portion of each of the multiple magnetic sensors,
an adjustment mechanism that is capable of switching between retraction of the multiple magnetic sensors from a detection position of leakage flux of the steel sheet and displacement of the multiple magnetic sensors to the detection position, and
a controller that controls application of an alternating current to the wiring for calibration and driving of the adjustment mechanism, wherein
each of the multiple magnetic sensors is connected in series to each of multiple gain-adjustable amplifiers and each of a bandpass filters extracting a frequency band to be detected,
the controller, while the sheet passing section does not pass the steel sheet, obtains a first output value of each of multiple magnetic sensors in advance by applying an alternating current to the wiring for calibration and inputting a pulse signal determining a frequency band corresponding to the alternating magnetic field generated by applying an alternating current to the bandpass filter, before a welded portion of the steel sheet that is passed by the sheet passing section passes a position of the magnetic sensors in a sheet passing direction while the sheet passing section passes the steel sheet, the controller retracts the multiple magnetic sensors from a detection position of leakage flux of the steel sheet, starts applying an alternating current to the wiring for calibration, inputting the pulse signal determining a frequency band corresponding to the alternating magnetic field generated by applying an alternating current to the bandpass filter, and obtains a second output value of each of the multiple magnetic sensors, and after the welded position passes the position of the magnetic sensors while the sheet passing section passes the steel sheet, the controller displaces the multiple magnetic sensors to the detection position, inputting the pulse signal corresponding to a certain pitch of an area where magnetic domain refining has been performed in the sheet passing direction of the steel sheet, and corrects a measurement value measured by each of the multiple magnetic sensors based on the first output value and the second output value.

6. The inspection device according to claim 5, wherein the wiring for calibration is arranged at a same relative position with respect to a magnetically sensitive portion of each of multiple magnetic sensors.

\* \* \* \* \*